(12) United States Patent
Buschnakowski et al.

(10) Patent No.: US 10,509,055 B2
(45) Date of Patent: Dec. 17, 2019

(54) METHOD FOR CONTACTING AT LEAST TWO METAL ELECTRODES AND ARRANGEMENT

(71) Applicant: Endress+Hauser Conducta GmbH+Co. KG, Gerlingen (DE)

(72) Inventors: Stephan Buschnakowski, Chemnitz (DE); Alexander Serfling, Leipzig (DE)

(73) Assignee: Endress+Hauser Conducta GmbH+Co. KG, Gerlingen (DE)

(*) Notice: Subject to any disclaimer, the term of this patent is extended or adjusted under 35 U.S.C. 154(b) by 0 days.

(21) Appl. No.: 16/101,643

(22) Filed: Aug. 13, 2018

(65) Prior Publication Data

US 2018/0348258 A1 Dec. 6, 2018

Related U.S. Application Data

(62) Division of application No. 14/479,537, filed on Sep. 8, 2014, now Pat. No. 10,073,118.

(30) Foreign Application Priority Data

Sep. 12, 2013 (DE) .................. 10 2013 110 044

(51) Int. Cl.
| | |
|---|---|
| *G01R 1/06* | (2006.01) |
| *G01R 1/073* | (2006.01) |
| *B23K 1/00* | (2006.01) |
| *B23K 1/20* | (2006.01) |
| *B32B 37/12* | (2006.01) |
| *G01N 27/07* | (2006.01) |
| *B23K 101/38* | (2006.01) |

(52) U.S. Cl.
CPC .......... *G01R 1/073* (2013.01); *B23K 1/0016* (2013.01); *B23K 1/20* (2013.01); *B32B 37/1284* (2013.01); *G01N 27/07* (2013.01); *B23K 2101/38* (2018.08)

(58) Field of Classification Search
CPC .......... G01R 1/06; G01R 1/073; G01R 27/02; G01R 27/22; G01R 27/26; G01R 27/28; G01R 27/221; G01R 27/30; G01R 27/08; G01R 31/2829; G01N 27/06; G01N 27/07
See application file for complete search history.

(56) References Cited

U.S. PATENT DOCUMENTS

| | | | | |
|---|---|---|---|---|
| 4,118,663 A * | 10/1978 | Barben, II | ............. | G01N 27/06 324/443 |
| 4,227,151 A * | 10/1980 | Ellis | ...................... | D06F 39/004 324/441 |
| 2002/0049385 A1* | 4/2002 | Booker | ................... | A61B 8/06 600/459 |
| 2004/0036476 A1* | 2/2004 | Brown | ................... | G01N 27/07 324/449 |

(Continued)

*Primary Examiner* — Thang X Le
(74) *Attorney, Agent, or Firm* — Mark A. Logan; PatServe

(57) ABSTRACT

The present disclosure discloses a conductivity sensor including a basic body of sintered ceramic having at least two cavities disposed on a frontal face and a metal electrodes disposed in each cavity. Each electrode is about one fifth the length of the basic body. Electrical cables extend from a rear face of the basic body into holes in each cavity and contact the electrodes. A solder paste or an electrically conductive adhesive disposed in each hole connects each cable with the respective metal electrode electrically and mechanically.

10 Claims, 2 Drawing Sheets

(56) References Cited

U.S. PATENT DOCUMENTS

| | | | | |
|---|---|---|---|---|
| 2004/0071945 A1* | 4/2004 | Ito | ............... | B32B 18/00 |
| | | | | 428/209 |
| 2011/0309848 A1* | 12/2011 | Eberheim | ............... | B22F 3/225 |
| | | | | 324/724 |
| 2013/0214797 A1* | 8/2013 | Gruden | ............... | D06F 39/004 |
| | | | | 324/663 |

* cited by examiner

METHOD FOR CONTACTING AT LEAST TWO METAL ELECTRODES AND ARRANGEMENT

CROSS-REFERENCE TO RELATED APPLICATIONS

The present divisional application is related to and claims the priority benefit of U.S. patent application Ser. No. 14/479,537, filed on Sep. 8, 2015 and German Patent Application No. 10 2013 110 044.9, filed Sep. 12, 2013, the entire contents of which are incorporated herein by reference.

TECHNICAL FIELD

The present disclosure relates to a method for contacting at least two metal electrodes as well as an arrangement comprising a contacting of at least two metal electrodes. The present disclosure relates further to a conductivity sensor comprising such an arrangement.

BACKGROUND

Known from the state of the art, for example, from Published International Application, WO 2010/072483, is a conductive conductivity sensor. This includes at least two electrodes, which when measuring are immersed in the measured medium. For determining the electrolytic conductivity of the measured medium, the resistance or conductance of the electrode measuring path in the measured medium is determined. In the case of known cell constant, the conductivity of the measured medium can then be ascertained therefrom. The electrodes are connected by means of a line or cable with a measurement transmitter, in which the conductivity is ascertained based on the measurement data.

The contacting of the electrodes to the line will now be explained based on FIG. 1. The electrodes 3 contact the measured medium at their ends 8 and extend from there rearwards through the basic body 2 and out the other side. The electrodes are there provided with connections 11, which are, in turn, connected with the measurement transmitter.

The connections 11 are either special plug- or screw contacts or in the simplest case cable is soldered to the connections 11. In both cases it is, however, necessary that the electrodes protrude out from the basic body. Since, most often, platinum is used as electrode material, this is very expensive.

SUMMARY

An object of the present disclosure is to provide a cost saving solution for contacting electrodes.

The object is achieved by a method, an arrangement and a conductivity sensor comprising such an arrangement.

As regards the method, the object is achieved in the context of features including that at least two metal electrodes are located in a cavity of a basic body of sintered ceramic and frontal end faces of the metal electrodes are arranged essentially planparallel to an outer surface of the basic body. The method includes steps as follows: introducing a solder means into at least one hole of the basic body, wherein the hole is so embodied that it leads to a rear portion of a metal electrode away from the frontal end face of the metal electrode, wherein the solder means can wet the rear portion of the metal electrode, wherein the metal electrodes are in their longitudinal direction shorter than the basic body, especially have only $\frac{1}{5}$ of the length of the basic body; introducing a cable into the hole at least until the cable extends into the solder means; and heating the basic body with solder means and cable above the solidification temperature of the solder means.

This provides, thus, an easy way of contacting the metal electrodes electrically and mechanically. Because of the short electrodes, costs are saved.

In an advantageous embodiment, the solder means is injected by means of air pressure into the hole. It is therewith possible to move the solder means into the hole right up to the rear end face of the metal electrode. Thus, for instance, a cartridge or cannula with a length, which corresponds at least to the depth of the hole, can be used.

Preferably, the hole is half filled with solder means. This has proven to be a sufficient amount for a stable contacting.

In a first advantageous further development, solder paste is used as solder means and the basic body, with solder means and cable, is heated above the melting temperature of the solder paste. In a second advantageous further development, electrically conductive adhesive is used as solder means and the basic body, with solder means and cable, is heated above the curing temperature of the electrically conductive adhesive.

As regards the arrangement, the object is achieved by an arrangement comprising: a basic body of sintered ceramic; at least two metal electrodes, wherein the metal electrodes are located in a cavity in the basic body and at least the frontal end faces of the metal electrodes are arranged essentially planparallel to an outer surface of the basic body, wherein the metal electrodes are shorter than the basic body, especially they are only $\frac{1}{5}$ of the length of the basic body, wherein the basic body has at least one hole, wherein the hole is so embodied that it leads to a rear portion of a metal electrode away from the frontal end face of the metal electrode; at least one cable, which extends into the hole, wherein a solder means, especially a solder paste, or an electrically conductive adhesive, connects the cable with the metal electrode electrically and mechanically. In a further development, as many holes are present as metal electrodes.

The end faces of the metal electrodes are planparallel to one another and/or to an outer surface of the basic body, while the end faces can be offset rearwards within the hole or extend frontally beyond the basic body.

In a preferred embodiment, the end faces of the metal electrodes are arranged flushly with the outer surface of the basic body. This facilitates a hygienic embodiment.

In all cases, the metal electrodes can contact the surrounding medium.

Preferably, the ceramic is zirconium dioxide and the metal electrodes are platinum electrodes. In a preferred embodiment, the zirconium dioxide is magnesium-, aluminum- or iridium stabilized.

In a first advantageous further development, at least one metal electrode is embodied as a cylinder, whose height essentially equals its diameter. In a second further development, at least one metal electrode is embodied as a hollow cylinder, whose height essentially equals its lateral thickness. An embodiment as a cylinder is especially advantageous, although other shapes, such as cuboid or especially cube, provide other options.

Preferably, two metal electrodes are provided and the metal electrodes are embodied as cylinders, or the metal electrodes are embodied as hollow cylinders, wherein the hollow cylinders are arranged concentrically.

Alternatively, four metal electrodes are provided and the metal electrodes are embodied as cylinders, wherein the cylinders are arranged in a row, or at least three metal electrodes are embodied as hollow cylinders, wherein the hollow cylinders are arranged concentrically and one metal electrode is arranged as a cylinder in the center of the hollow cylinders.

In an advantageous form of embodiment, the cable includes an insulation, especially a polytetrafluoroethylene coating, wherein the insulation is removed in the part of the cable contacting the solder means.

The object is further achieved by a conductivity sensor, especially by a conductive conductivity sensor, comprising an arrangement as described above.

BRIEF DESCRIPTION OF THE DRAWINGS

The present disclosure will now be explained in greater detail based on the appended drawing, the figures of which show as follows.

Figure 1:
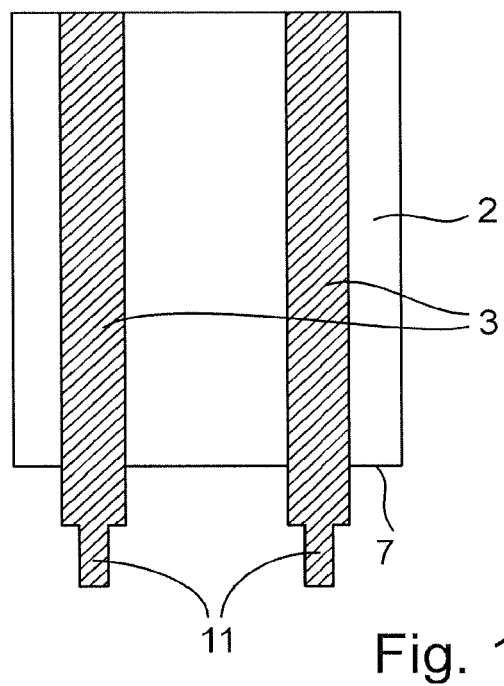
FIG. 1 shows the state of the art.

In the figures, equal features are provided with equal reference characters.

DETAILED DESCRIPTION

The present disclosure will be explained based on a conductivity sensor, especially based on a conductive conductivity sensor. The basic idea is, however, applicable also to other types of sensors that use metal electrodes. Other options include the most varied of sensors from the field of process automation, such as, for instance, pH-sensors, amperometric sensors, etc.

Figure 2:
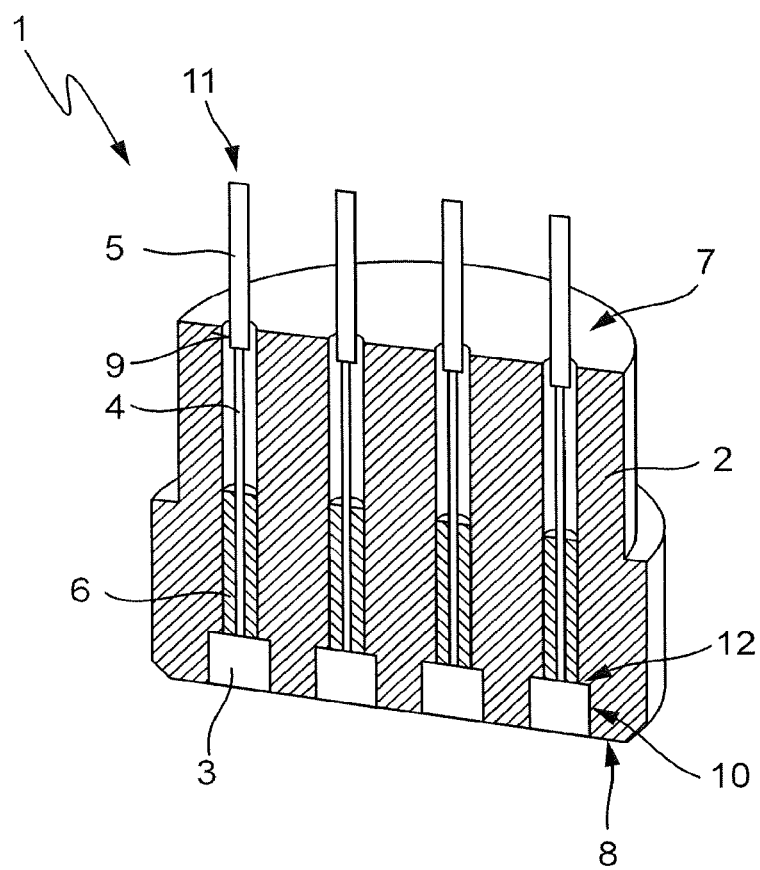
FIG. 2 shows in cross section a first embodiment of the arrangement of the present disclosure.
Figure 3:
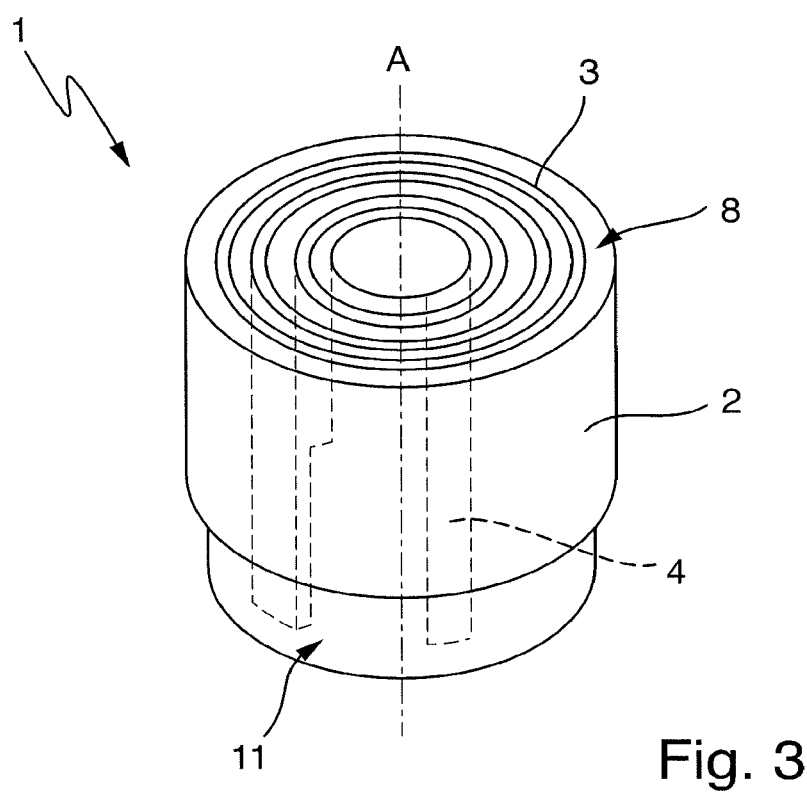
FIG. 3 shows in cross section a second embodiment of the arrangement of the present disclosure.

The arrangement 1 of the present disclosure can thus be part of a conductivity sensor. FIGS. 2 and 3 show a conductivity sensor, with a basic body 2 of a ceramic such as, for instance, zirconium dioxide, thus generally of an electrically non-conductive material. In an embodiment, the zirconium dioxide is stabilized with magnesium, aluminum, or iridium. Embedded in the basic body 2, more exactly in a cavity 10 thereof, are metal electrodes 3, for instance, of platinum. The electrodes 3 and the basic body 2 form a composite material, i.e. are, for instance, sintered together. In this way, no measured medium can penetrate into the interior of the basic body 2. At the end face 8 of the basic body 2, the frontal end faces of the electrodes 3 lie freely exposed and in the case of a measuring of conductivity contact the measured medium. Advantageously, the end faces of the electrodes 3 and the end faces of the basic body are flush with one another, i.e. lie in the same plane. However, the electrodes can also protrude out from the basic body 2 or be arranged sunken in the basic body 2.

The arrangement 1 shown in FIGS. 2 and 3 forms the measuring probe of a so-called 4-electrode sensor. The probe is immersible in a measured medium. Two of the electrodes 3, especially two electrodes 3 directly adjoining one another, are operated as so called electrical current electrodes. The two remaining electrodes 3 are operated as so called voltage electrodes. An alternating voltage is applied between the two electrical current electrodes in measurement operation and therewith an alternating electrical current is caused to flow in the measured medium. Measured, especially by a currentless measuring, between the voltage electrodes is the resulting potential difference. From the introduced alternating electrical current and the measured potential difference, the impedance of the conductivity measurement cell formed by immersion of the arrangement 1 in a measured medium is calculated, from which, taking into consideration the cell constant, the specific resistance, respectively the conductivity, of the measured medium can be ascertained. Serving for control of the supplied alternating current, for measuring the potential difference of the voltage electrodes and for converting the measured values into a resistance-, respectively conductance, or a specific resistance, respectively specific conductivity, of the measured medium, is a measurement transmitter (not shown) connected with the arrangement 1. The connection is accomplished, for instance, via connections 11. The measuring electronics can be a component of the measurement transmitter or be at least partially accommodated in a separate module, for example, in a plug head connected with the arrangement 1. The ascertained measured values can either be displayed by the measurement transmitter or output to a superordinated control system. Alternatively to a measurement transmitter, the measured values can also be transmitted directly to a bus; in that way, the arrangement is directly connected with the control system.

Alternatively to a 4-electrode sensor, also a 2-electrode sensor provides an option. The construction is, in such case, basically equal. In the case of a 2-electrode sensor, in measurement operation, an alternating voltage is applied to the two electrodes 3. Using a measurement transmitter (not shown) connected with the electrodes 3, the impedance of the conductivity measurement cell formed by the measuring probe immersed in the measured medium is ascertained. Taking into consideration the cell constants, the specific resistance, respectively the specific conductivity, of the measured medium can be ascertained therefrom. The ascertained measured values can either be displayed by the measurement transmitter or output to a superordinated control system. A part of the functions of the measurement transmitter can be executed by a measuring electronics accommodated in a separate housing outside of the measurement transmitter. This measuring electronics can at least in part, be accommodated, for example, in a plug head connected with the arrangement 1.

In FIG. 2, respectively FIG. 3, for reasons of perspicuity, only one of the electrodes is provided with reference characters.

In FIG. 2, the electrodes 3 are embodied as cylinders. Compared with the length of the basic body, the electrodes are very much shorter. They are, for instance, only ⅕ of the length of the basic body. As an example, the basic body 2 has a height of 10 mm. The electrodes 2 then have a length of, for instance, 1 mm to 3 mm, for example, 2 mm or less, for instance, 1.5 mm.

FIG. 3 shows an alternative embodiment for conductive conductivity measurement, in the case of which the electrodes 3 are hollow cylinders arranged coaxially about a shared rotational symmetry axis A and embedded insulated from one another in the basic body 2. The central electrode 3 is embodied as a solid cylinder. The electrodes 3 lie on the end face 8 of the basic body 2 with their annular end faces freely exposed. The height of the hollow cylinders essentially equals their wall thickness. Compared with the length of the basic body 2, thus, also in this embodiment, the electrodes 3 are clearly shorter.

The contacting of the electrodes occurs in all cases (two/four electrodes, solid cylinder/hollow cylinder electrodes) equally and will now be explained as follows.

Holes 9 lead from the rear-side of the basic body to the electrodes 3.

With the help of air pressure, solder means 6 is introduced into these holes 9. Used for this procedure is, for instance, a cartridge or cannula with a length equaling at least the depth of the holes 9.

The solder means 6 can wet at least the electrode 3. It has been found to be advantageous to fill the holes 9, for instance, half way with solder means 6. The solder means is a solder paste or a conductive adhesive.

Then a cable 4 is brought into the hole 9 sufficiently that a part of the cable 4 extends into the solder means 6. Since the solder means 6 is sticky, first a mechanical connection is formed.

The cable has an insulation 5, for example, of Teflon polymer, which is, however, removed from the part of the cable 4 contacting the solder means.

In the next step, the basic body 2 with the cable 4 and the solder means 6 is heated above the solidification temperature of the solder means 6. This can be accomplished, for instance, in a furnace, for example, in a high frequency oven. Alternatively, a heated support can be used.

In the case of application of solder paste as solder means 6, the solidification temperature is understood to be the melting temperature of the solder paste. In such case, the individual particles of the paste melt and coalesce and, in each case, upon cooling form a mechanically stable connection as well as an electrical connection of electrode 3 to cable 4. Additionally, the volatile part of the flux of the solder paste evaporates out the hole. Possible differences of thermal coefficients of expansion of the different materials scarcely play a role, since the solder means can expand in the direction of the length of the hole 9. A typical melting temperature is, for instance, 260° C.

In the case of application of electrically conductive adhesives as solder means 6, the solidification temperature is understood to be the curing temperature of the adhesive.

The melting of the solder means 6 leads to an electrical (low ohm) and mechanical connection between electrode 2 and cable 4.

The invention claimed is:

1. An arrangement, comprising:
a body of sintered ceramic, the body having a front face and a rear face and two cavities disposed in the front face, each of the two cavities having a through-hole leading from the respective cavity, through the body, to the rear face;
two metal electrodes, wherein each metal electrode is disposed in a cavity of the two cavities in the body such that a front end face of each metal electrode is essentially plan-parallel to the front face of the body;
two electrical cables, wherein each electrical cable extends from outside the body into the rear face of the body and into a through-hole of the two through-holes; and
a solder paste or an electrically conductive adhesive disposed in each through-hole such that the solder paste or electrically conductive adhesive connects each cable with the respective metal electrode electrically and mechanically,
wherein the two metal electrodes are embodied as hollow cylinders, each hollow cylinder having a height and a wall thickness, wherein the height of each hollow cylinder is substantially equal to its wall thickness, wherein the two hollow cylinders are disposed concentrically.

2. The arrangement as claimed in claim 1, wherein the frontal end face of each metal electrode is flush with the front face of the body.

3. The arrangement as claimed in claim 1, wherein the ceramic is zirconium dioxide and the two metal electrodes are platinum.

4. The arrangement as claimed in claim 3, wherein the zirconium dioxide is stabilized with one of the following: magnesium, aluminum, and iridium.

5. The arrangement as claimed in claim 1, wherein the two electrical cables include a polytetrafluoroethylene coating, wherein the polytetrafluoroethylene coating is not present in a part of the cable contacting the solder paste or the electrically conductive adhesive.

6. The arrangement as claimed in claim 1, wherein each metal electrode is about one fifth a length of the body.

7. An arrangement, comprising:
a body of sintered ceramic, the body having a front face and a rear face and four cavities disposed in the front face, each of the four cavities having a through-hole leading from the respective cavity, through the body, to the rear face;
four metal electrodes, wherein each metal electrode is disposed in a cavity of the four cavities in the body such that a front end face of each metal electrode is essentially plan-parallel to the front face of the body;
four electrical cables, wherein each electrical cable extends from outside the body into the rear face of the body and into a through-hole of the four through-holes; and
a solder paste or an electrically conductive adhesive disposed in each through-hole such that the solder paste or electrically conductive adhesive connects each cable with the respective metal electrode electrically and mechanically,
wherein each of the four metal electrodes is embodied as a cylinder, each cylinder having a height and a diameter, wherein the height of each cylinder is substantially equal its diameter, and wherein the four cylinders are arranged in a row.

8. The arrangement as claimed in claim 7, wherein each metal electrode is about one fifth a length of the body.

9. An arrangement, comprising:
a body of sintered ceramic, the body having a front face and a rear face and four cavities disposed in the front face, each of the four cavities having a through-hole leading from the respective cavity, through the body, to the rear face;
four metal electrodes, wherein each metal electrode is disposed in a cavity of the four cavities in the body such that a front end face of each metal electrode is essentially plan-parallel to the front face of the body;
four electrical cables, wherein each electrical cable extends from outside the body into the rear face of the body and into a through-hole of the four through-holes; and
a solder paste or an electrically conductive adhesive disposed in each through-hole such that the solder paste or electrically conductive adhesive connects each cable with the respective metal electrode electrically and mechanically,
wherein a first metal electrode of the four metal electrodes is embodied as a cylinder having a height and a diameter substantially equal to each other, wherein the remaining three metal electrodes of the four metal electrodes are embodied as hollow cylinders, each hollow cylinder having a height and a wall thickness, wherein the height of each hollow cylinder is substantially equal its wall thickness, and wherein the four metal electrodes are arranged concentrically centered about the first metal electrode.

10. The arrangement as claimed in claim 9, wherein each metal electrode is about one fifth a length of the body.

* * * * *